United States Patent
DeLeo

(10) Patent No.: US 7,763,626 B2
(45) Date of Patent: Jul. 27, 2010

(54) COMPOSITIONS AND METHOD FOR ENHANCING THE THERAPEUTIC ACTIVITY OF OPIODS IN TREATMENT OF PAIN

(75) Inventor: Joyce A. DeLeo, Lebanon, NH (US)

(73) Assignee: Trustees of Dartmouth College, Hanover, NH (US)

(*) Notice: Subject to any disclaimer, the term of this patent is extended or adjusted under 35 U.S.C. 154(b) by 1016 days.

(21) Appl. No.: 11/129,790

(22) Filed: May 16, 2005

(65) Prior Publication Data
US 2005/0282832 A1  Dec. 22, 2005

Related U.S. Application Data

(60) Provisional application No. 60/580,876, filed on Jun. 18, 2004.

(51) Int. Cl.
*A61K 31/522*  (2006.01)
*A61K 31/485*  (2006.01)
*A61P 25/30*  (2006.01)

(52) U.S. Cl. .................. 514/263.32; 514/282
(58) Field of Classification Search ............ 514/263.32, 514/282
See application file for complete search history.

(56) References Cited

U.S. PATENT DOCUMENTS

| | | | | |
|---|---|---|---|---|
| 6,124,323 | A * | 9/2000 | Bigge et al. | 514/327 |
| 6,413,976 | B1 * | 7/2002 | DeLeo et al. | 514/263.36 |
| 2003/0040486 | A1 * | 2/2003 | Demopulos et al. | 514/19 |

FOREIGN PATENT DOCUMENTS

JP         09221423    *   8/1997

OTHER PUBLICATIONS

Raghavendra, "Attenuation of Morphine Tolerance, Withdrawal-Induced Hyperalgesia, and Associated Spinal Inflammatory Immune Responses by Propentofylline in Rats", Neuropsychopharmacology, 2004, 29, 327-334.*
Beitner-Johnson et al., "Glial Fibrillary Acidic Protein and the Mesolimbic Dopamine System:Regulation by Chronic Morphine and Lewis-Fischer Strain Differences in the Rat Ventral Tegmental Area", Journal of Neurochemistry 1993 61:1766-1773.
Bian et al., "Loss of antiallodynic and antinociceptive spinal/supraspinal morphine synergy in nerve-injured rats:restoration by MK-801 or dynorphin antiserum", Brain Research 831 1999 55-63.
Chao et al., "Priming Effect of Morphine on the Production of Tumor Necrosis Factor-α by Microglia:Implications in Respiratory Burst Activity and Human Immunodeficiency Virus-1 Expression[1]", J. Pharmacology and Experimental Therapeutics 1994 269(1):198-203.
Chao et al., "Activation of *Mu* Opioid Receptors Inhibits Microglial Cell Chemotaxis[1]", J. Pharmacology and Experimental Therapeutics 1997 281(2):998-1004.
DeLeo et al., "Propentfylline (HWA 285) protects hippocampas neurons of Mongolian gerbils against ischemic damage in the presence of an adenosine antagonist", Neuroscience Letters 84 1998 307-311.
Hu et al., "Morphine induces apoptosis of human microglia and neurons", Neuropharmacology 42 2002 839-836.
Johnston et al., "B13-Opioid Action-(803) Role of glial interleukin 1 in morphine analgesia and analgesic tolerance", J. Pain 4(2, suppl 1):52.
Kamada et al., "Up-regulation of NGF, trkA, Fas, Down-Regulation of bcl-2, and Induction of Apoptosis by Propentofylline in Human Glioma Cell Lines", Brain & Nerve 1996 48:1022-1028.
Kwon et al., "Pharmacokinetics of Propentofylline and the Quantitation of Its Metabolite Hydroxypropentofylline in Human Volunteers", Arch. Pharm. Res. 1998 21:698-702.
Mao et al., "Mechanisms of hyperalgesia and morphine tolerance:a current view of their possible interactions", Pain 1995 62:259-274.
Mayer et al., "Cellular mechanisms of neuropathic pain, morphine tolerance, and their interactions", Proc. Natl. Acad. Sci. USA 1999 96:7731-7736.
Mielke et al., "Propentofylline in the Treatment of Vascular Dementia and Alzheimer-Type Dementia:Overview of Phase I and Phase II Clinical Trials", Alzheimer Disease and Associated Disorders 1999 12(2):S29-S35.
Miki et al., "Differential Effects of Propentofylline on the Production of Cytokines by Peripheral Blood Mononuclear Cells in Vitro", Clinical Therapeutics 1991 13(6):747-753.
Ossipov et al., "Induction of pain facilitation by sustained opioid exposure:relationship to opioid antinociceptive tolerance", Life Sciences 2003 73:783-800.
Raghavendra et al., "The Role of Spinal Neuroimmune Activation in Morphine Tolerance/Hyperalgesia in Neuropathic and Sham-Operated Rats", The Journal of Neuroscience 2002 22(22):9980-9989.
Rother et al., "Propentofylline in the Treatment of Alzheimer's Disease and Vascular Dementia:A Review of Phase III Trials", Dement Geriatr Cogn Disord 1998 9(1):36-43.
Schubert et al., "Support of Homeostatic Glial Cell Signaling:A Novel Therapeutic Approach by Propentofylline", Ann. NY Acad. Sci. 1997 826:337-347.
Song et al., "The involvement of glial cells in the development of morphine tolerance", Neuroscience Research 2001 39:281-286.
Sweitzer et al., "Propentofyllne, a Glial Modulating Agent, Exhibits Antiallodynic Properties in a Rat Model of Neuropathic Pain", Journal of Pharmacology and Experimental Therapeutics 2001 297(3):1210-1217.

* cited by examiner

*Primary Examiner*—Sreeni Padmanabhan
*Assistant Examiner*—Sahar Javanmard
(74) *Attorney, Agent, or Firm*—Licata & Tyrrell P.C.

(57) ABSTRACT

Compositions and methods for inhibiting opioid tolerance and opioid withdrawal-induced hyperalgesia are provided.

2 Claims, 1 Drawing Sheet

COMPOSITIONS AND METHOD FOR ENHANCING THE THERAPEUTIC ACTIVITY OF OPIODS IN TREATMENT OF PAIN

INTRODUCTION

This application claims the benefit of U.S. Provisional Application No. 60/680,876 filed Jun. 18, 2004, which is herein incorporated by reference in its entirety.

This invention was made with government support under Grant No. DA11276 awarded by the National Institutes of Health. Therefore, the U.S. government may have certain rights in the invention.

BACKGROUND OF THE INVENTION

Chronic pain from nerve injury is a debilitating condition that affects millions of Americans. Such pain can occur as a result of cancer, multiple sclerosis, HIV-associated neuropathy, diabetic neuropathy, trigeminal neuralgia, postherpetic neuralgia (shingles), phantom limb pain, nerve injury due to trauma or surgery, and deafferentation pain. Most of these chronic pain syndromes are refractory to standard analgesics such as morphine and non-steroidal anti-inflammatory drugs. In addition, such drugs must be given in high doses such that they are associated with a variety of side effects that often limits the long-term use. Many of these side effects are life-threatening such as kidney toxicity and gastrointestinal distress in the case of the non-steroidal anti-inflammatory drugs and respiratory depression in the case of morphine.

In addition to the known toxicities of opioids, morphine, and other opioids used as standards of care for pain treatment, also can be limited in their therapeutic use by the development of hyperalgesia and tolerance. Both of these conditions lead to a failure of opioid therapy to produce pain relief in patients, which can be debilitating. Neuronal plasticity associated with hyperalgesia and morphine tolerance has similar cellular and molecular mechanisms, suggesting predictable interactions between hyperalgesia and morphine tolerance (Mao, J. et al. 1995. *Pain* 62:259-274; Mayer, D. J. et al. 1999. *Proc. Natl. Acad. Sci. USA* 96:7731-7736). The induction of pain facilitation by sustained opioid exposure contributes to the development of opioid anti-nociceptive tolerance, and manipulations that block enhanced pain also block anti-nociceptive tolerance (Ossipov, M. H. et al. 2003. *Life Sci.* 73:783-800). The role of glia and their secretory products, particularly pro-inflammatory cytokines, in the development of morphine tolerance, and morphine-withdrawal-induced hyperalgesia, have been recently studied (Song, P. And Z-Q. Zhao. 2001. *Neurosci. Res.* 39:281-286; Raghavendra, V. et al. 2002. *J. Neurosci.* 22:9980-9989). Both glial (microglia and astrocyte) activation and enhanced pro-inflammatory cytokine levels were observed following chronic morphine treatment at the lumbar spinal cord of the rat (Raghavendra, V. et al. 2002. *J. Neurosci.* 22:9980-9989). Inhibition of astrocyte activation or antagonizing the activity of pro-inflammatory cytokines (interleukin-1β, interleukin-6 and tumor necrosis factor-α) attenuated the development of morphine tolerance, and withdrawal-induced hyperalgesia in rats (Song, P. And Z-Q. Zhao. 2001. *Neurosci. Res.* 39:281-286; Raghavendra, V. et al. 2002. *J. Neurosci.* 22:9980-9989; Johnston, I. et al. 2003. *J. Pain* 4(S1):52).

Propentofylline is a xanthine derivative that has been tested extensively in humans as a neuroprotective agent for treatment of Alzheimer's Disease and vascular dementia. It has a different pharmacological profile than other classical methylxanthines including theophylline and caffeine. In clinical trials, propentofylline has been shown to be both safe and effective for the treatment of these neurodegenerative diseases (Mielke et al., *Alzheimer Dis. Assoc. Disord.*, 1998, 12, S29-35; Rother et al., *Dement. Geriatr. Cogn. Disord.*, 1998, 9, 36-43). The effects observed with propentofylline treatment include a reduction in the extent of brain neuropathology, an improvement in cognitive function, a decrease in activation of microglia, and inhibition of inflammatory processes. The drug is well absorbed and extensively metabolized following oral dosing (Kwon et al., *Arch. Pharm. Res.*, 1998, 21, 698-702). The pharmacokinetic and pharmacodynamic profile of propentofylline have made it a promising therapeutic in the treatment of neurodegenerative diseases.

The pharmacological effects of propentofylline have been linked to inhibition of adenosine transport and inhibition of phosphodiesterase. Studies have also suggested this drug has effects to stimulate the synthesis and secretion of nerve growth factor, and can act as a transcriptional modulator and inducer of apoptosis in certain types of brain cells (Kamada et al., *No To Shinkei*, 1996, 48, 1022-1028). Propentofylline has also been shown to have a differential effect on the production of certain cytokines such as interleukin-6, interleukin-1 beta, and tumor necrosis factor alpha (Miki et al., *Clin. Ther.*, 1991, 13, 747-753). It is known as well to modulate glial activity under pathological conditions. Propentofylline depresses the activation of microglia and astrocytes, which are associated with neuronal damage during ischemic injury (DeLeo, J. et al. 1988. *Neurosci. Lett.* 84:307-311; Schubert, P. et al. 1997. *Ann. NY Acad. Sci.* 826:337-347).

Studies have shown that propentofylline is capable of attenuating nerve injury-induced hyperalgesia in rats (Sweitzer, S. M. et al. 2001. *J. Pharmacol. Exp. Ther.* 297: 1210-1217). Although the specific mechanism of propentofylline-induced effects on hyperalgesia remains unknown, several actions have been proposed. Propentofylline has been shown to inhibit adenosine transport and the cyclic-adenosine-5',3'-monophosphate (cAMP)-specific phosphodiesterase (PDE IV) leading to the induction of cAMP (Meskini et al. 1994; Nagata et al. 1985; Parkinson and Fredholm 1991). Strengthening of cAMP-dependent signaling decreases microglial proliferation and activation in culture (Si et al. 1996), providing a possible mechanism for propentofylline-induced glial modulation. Glial activation and increased pro-inflammatory cytokines are observed during morphine tolerance and withdrawal-induced hyperalgesia.

Glial cells contribute to synaptic homeostasis by releasing neurotrophic factors, promoting synaptogenesis and preventing glutamate excitotoxicity by promoting Na+-dependent glutamate uptake (Liberto et al. 2004). To date, five glutamate transporter subtypes have been identified (Danbolt 2001). EAAT1/GLAST and EAAT2/GLT-1 are thought to be primarily localized to astrocytes although they have recently been demonstrated to be expressed on (Lopez-Redondo et al. 2000) and neurons (Chen et al. 2004). In vitro, activated astrocytes have been shown to express low levels of GLT-1 which are enhanced upon dibutyryl-cAMP (db-cAMP) stimulation-induced differentiation (Schlag et al. 1998). Activated astrocytes may lose their homeostatic functions upon exposure to stressors and increase the expression of cytokines, nitric oxide and prostaglandins as an injury response (Watkins et al. 2001). Prior studies have determined that 7 days post-chronic constriction injury (Sung et al. 2003), or facial nerve axotomy (Lopez-Redondo et al. 2000), glial glutamate transporters are decreased corresponding temporally to our observation of enhanced astrocytic activation (Sweitzer et al. 2001; Tanga et al. 2004).

It has now been found that propentofylline, a drug shown to have a favorable safety profile in humans with neurodegenerative disease, has the ability to attenuate the development of hyperalgesia and the expression of analgesic tolerance to opioids, such as morphine.

SUMMARY OF THE INVENTION

An object of the present invention is a pharmaceutical composition for inhibition of opioid tolerance and opioid withdrawal-induced hyperalgesia which comprises propentofylline, an opioid drug, and a pharmaceutically acceptable carrier. In one embodiment the opioid drug is morphine.

Another object of the present invention is a method for inhibiting opioid tolerance and opioid withdrawal-induced hyperalgesia in an animal which comprises administering to an animal the pharmaceutical composition of the instant invention so that opioid tolerance and opioid withdrawal-induced hyperalgesia is inhibited. In one embodiment of this method, the opioid drug administered is morphine.

Yet another object of the present invention is a method for decreasing the effective dose of an opioid drug in an animal which comprises administering to an animal the pharmaceutical composition of the instant invention so that the effective dose of the opioid drug is decreased. In one embodiment of the method, the opioid drug is morphine.

DETAILED DESCRIPTION OF THE INVENTION

Figure 1A:
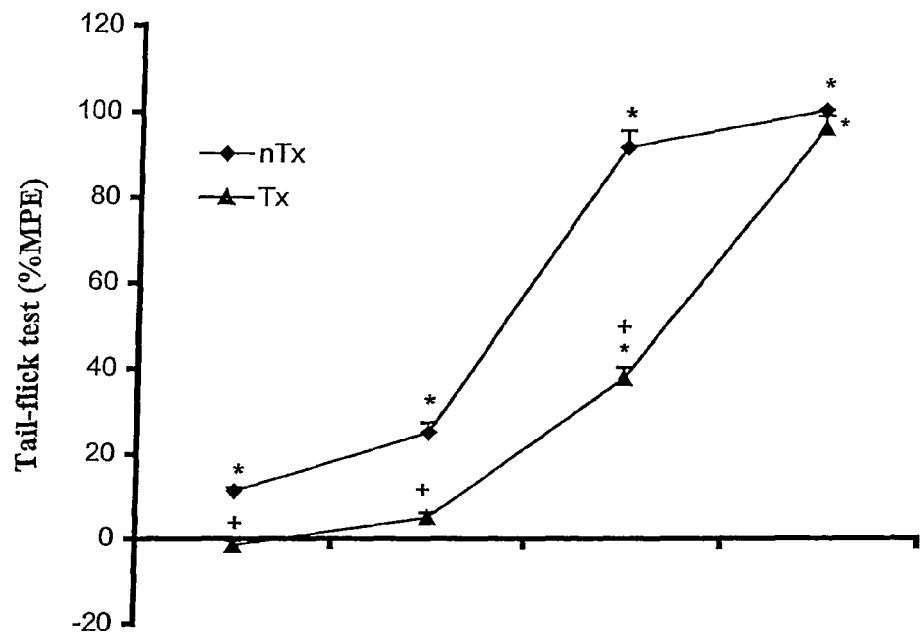
FIG. 1A is a graph of tail-flick test results from subcutaneous morphine administration demonstrating an anti-nociceptive tolerance to acute intrathecal morphine.

Chronic pain from nerve injury (neuropathic) includes but is not limited to conditions such as pain associated with cancer, chemotherapy-induced pain, pain due to multiple sclerosis, HIV-associated neuropathy, diabetic neuropathy, trigeminal neuralgia, postherpetic neuralgia (shingles), phantom limb pain, nerve injury caused by surgery or trauma, deafferentation pain, and low back pain. Neuropathic pain is not only chronic and intractable, but is debilitating and can cause extreme physical, psychological and social distress and suffering.

Opioids are the most effective analgesics used to treat many forms of neuropathic chronic pain. The clinical use of opioid analgesics is often hampered by the development of analgesic tolerance that necessitates dose escalation regardless of the disease progression. It has been shown previously that glial activation and subsequent pro-inflammatory immune responses at the lumbar spinal cord contribute to the development of morphine tolerance and morphine withdrawal-induced hyperalgesia (Song, P. And Z-Q. Zhao. 2001. *Neurosci. Res.* 39:281-286; Raghavendra, V. et al. 2002. *J. Neurosci.* 22:9980-9989; Johnston, I. et al. 2003. *J. Pain* 4(S1):52). It has now been found that co-administration of morphine or other opioids with propentofylline may prevent dose escalation of the opioid, increase opioid efficacy in neuropathic pain and prevent tolerance, opioid-induced pain and opioid withdrawal-induced pain (hyperalgesia).

Experiments were performed using a well-established animal model for morphine tolerance and withdrawal-induced hyperalgesia (Raghavendra, V. et al. 2002. *J. Neurosci.* 22:9980-9989). Male Sprague-Dawley rats (175-200 grams, Harlan, Indianapolis, Ind.) were divided into two groups (n=8 per group). Rats received subcutaneous injections of either saline or morphine (10 mg/kg; Sigma, St. Louis, Mo.) twice daily at 0800 to 0900 and 1600-1700 hour for 5 days in order to induce opioid tolerance. Chronic morphine withdrawal-induced hyperalgesia and allodynia were assessed in the animals 16 hours after the last injection of morphine. Following the recording of morphine withdrawal-induced hyperalgesia and allodynia, animals were treated with morphine (5 microgram) acutely via lumbar intrathecal injection to study the expression of morphine tolerance. Acute analgesic activity or intrathecal morphine in morphine-tolerant and chronic aline-treated rats were evaluated by mechanical (Analgesy-Meter) and thermal (tail-flick) test paradigms. Behaviors recorded prior to the acute administration of intrathecal morphine served as the basal latency measures. The results showed that chronic administration of morphine led to withdrawal-induced thermal and mechanical hyperalgesia and mechanical allodynia when recorded 16 hours after the last morphine injection.

With an understanding of the effects of morphine alone, separate groups of rats (n=8) received with saline or morphine (10 mg/kg subcutaneously, twice daily for 5 days) and also received once daily injections (at 1100 to 1200 hour) of propentofylline (1 and 10 micrograms) or saline via direct lumbar puncture during the induction of morphine tolerance. Again, chronic morphine withdrawal-induced hyperalgesia and allodynia were assessed in the animals 16 hours after the last subcutaneous morphine injection. Following the recording of morphine withdrawal-induced hyperalgesia and allodynia, animals were treated with morphine (5 micrograms) acutely via lumbar puncture to study the expression of morphine tolerance. As before, the acute analgesic activity of intrathecal morphine in morphine-tolerant and saline-injected rats was evaluated by mechanical (Analgesy-Meter) and thermal (tail-flick) test paradigms. Behavior recorded prior to the acute administration of intrathecal morphine served as the basal latency. Chronic propentofylline treatment (10 micrograms intrathecally for 5 days) had no effect on the nociceptive threshold in the saline-treated rats. However, propentofylline administration (1 and 10 micrograms intrathecally for 5 days) given during induction of morphine tolerance significantly attenuated morphine withdrawal-induced noxious thermal and mechanical hyperalgesia, as well as mechanical allodynia (see Table 1).

TABLE 1

Effect of Propentofylline on Morphine Withdrawal-induced Hyperalgesia and Allodynia

| Treatment | Tail-flick latency (seconds) | Paw pressure latency (grams) | Mechanical allodynia (2 grams) | Mechanical allodynia (12 grams) |
|---|---|---|---|---|
| Saline | 5.3 ± 0.02 | 113.5 ± 4.2 | 0 | 0.1 ± 0.2 |
| Saline + propentofylline (10 micrograms) | 5.1 ± 0.3 | 119.4 ± 5.4 | 0 | 0 |
| Morphine | 3.7 ± 0.2* | 69.8 ± 4.8* | 3.9 ± 0.5* | 6.9 ± 0.7* |
| Morphine + propentofylline (1 microgram) | 4.6 ± 0.2# | 85.4 ± 5.9# | 1.6 ± 0.2# | 2.4 ± 0.4# |

TABLE 1-continued

Effect of Propentofylline on Morphine Withdrawal-induced Hyperalgesia and Allodynia

| Treatment | Tail-flick latency (seconds) | Paw pressure latency (grams) | Mechanical allodynia (2 grams) | Mechanical allodynia (12 grams) |
|---|---|---|---|---|
| Morphine + propentofylline (10 micrograms) | 4.9 ± 0.2# | 96.3 ± 4.7# | 1.2 ± 0.3# | 1.8 ± 0.6# |

*indicates statistically significant difference from the saline control group, p < 0.05
indicates statistically significant difference from the Morphine treated group, p < 0.05

Figure 1B:
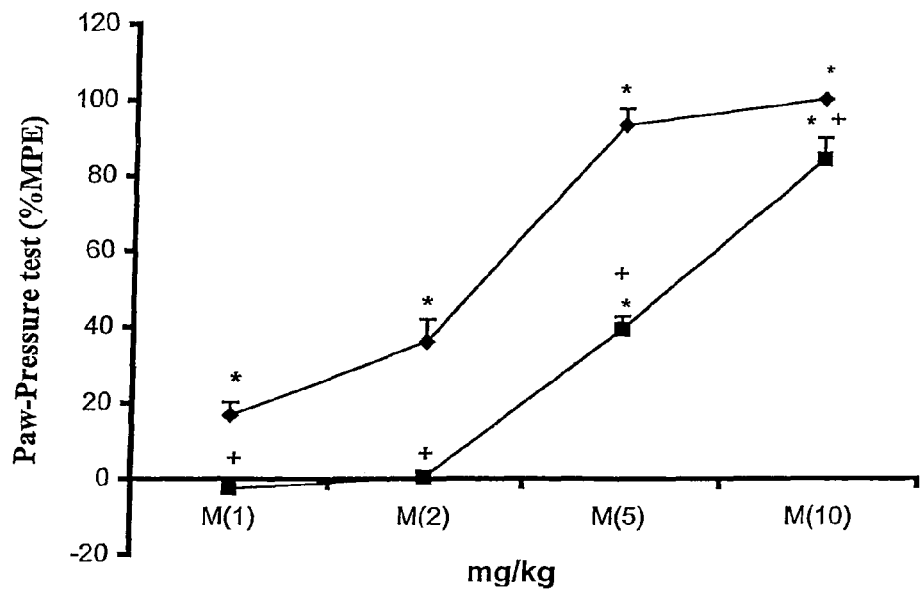
FIG. 1B is a graph of paw-pressure test results from subcutaneous morphine administration demonstrating an antinociceptive tolerance to acute intrathecal morphine.

Chronic administration of subcutaneous morphine (10 mg/kg. Twice daily for 5 days) demonstrated anti-nociceptive tolerance to acute intrathecal morphine (5 micrograms) in both noxious thermal and mechanical testing paradigms (FIG. 1). Propentofylline treatment (10 micrograms intrathecally for 5 days) in chronic saline-treated rats (subcutaneous, twice daily for 5 days) had no effect on the anti-nociceptive activity of acute intrathecal morphine (5 micrograms). However, propentofylline (1 and 10 micrograms intrathecally for 5 days), when given during the induction of morphine tolerance (10 mg/kg subcutaneously, twice daily for 5 days) the drug significantly attenuated the expression of spinal nociceptive tolerance to intrathecal morphine (5 micrograms) in both noxious thermal and mechanical test paradigms (FIG. 1).

In previous studies, chronic morphine treatment had been shown to significantly elevate the levels of immunoreactive OX-42 and glial fibrillary acidic protein (GFAP) at the dorsal horn of the L5 lumbar spinal cord (Song, P. And Z-Q. Zhao. 2001. Neurosci. Res. 39:281-286; Raghavendra, V. et al. 2002. J. Neurosci. 22:9980-9989). Experiments were now performed to determine whether propentofylline treatment had an effect on these types of cellular changes induced by chronic morphine administration. Real-time RT-PCR, RNase protection assay, and ELISA were used to examine changes in mRNA levels of GFAP, macrophage antigen complex-1 (Mac-1) and cytokines, as well as cytokine protein levels. A separate group of rats (n=4) was used that had been treated with propentofylline and morphine as described above. After behavioral testing for reactions to the combined treatment, rats were sacrificed and decapitated. An 18-gauge needle was inserted into the caudal end of the vertebral column and the spinal cord was expelled with ice-cold phosphate-buffered saline. The spinal cord was frozen immediately on dry ice and stored at −80° C. until homogenization. The L5 lumbar spinal cord was isolated from the intact frozen cord at the time of mRNA and protein quantification. Total RNA was isolated from the L5 spinal cord by the TRIzol extraction method (Invitrogen Corporation, Carlsbad, Calif).

Using the real-time PCR technique, significant increases in Mac-1 and GFAP mRNA levels were observed at the L5 lumbar spinal cord of chronic morphine-treated rats (10 mg/kg, twice daily for 5 days) compared to saline-treated controls (FIG. 2). Propentofylline (10 micrograms intrathecally for 5 days) had no effect on the expression of Mac-1 and GFAP in saline-treated rats. However, propentofylline administration during the induction phase of morphine tolerance significantly attenuated chronic morphine-induced upregulation of Mac-1 and GFAP (FIG. 2).

The effects of propentofylline on morphine-induced cytokine mRNA levels and protein levels were also examined. Chronic administration of morphine (10 mg/kg twice daily for 5 days) significantly increased the expression of mRNA and protein levels of interleukin-1β (IL-1β) and interleukin-6 (IL-6) at the L5 lumbar spinal cord compared to saline-treated rats (Tables 2 and 3). Although morphine treatment significantly enhanced the expression of tumor necrosis factor-alpha (TNF-α) mRNA, protein levels of this cytokine were not significantly increased when compared to chronic saline-treated animals. Propentofylline treatment (10 micrograms intrathecally for 5 days) had no significant effect on the expression of IL-1β, IL-6 and TNF-α in saline-treated rats but significantly attenuated morphine-induced mRNA upregulation for IL-1β, IL-6 and TNF-α mRNA and protein levels during the induction of morphine tolerance (Tables 2 and 3).

TABLE 2

Effect of Propentofylline (10 μg) on Chronic Morphine-Induced Upregulation of mRNA for IL-1β, IL-6 and TNF-α at the L5 Lumbar Spinal Cord

| Treatment | IL-1β | IL-6 | TNF-α |
|---|---|---|---|
| Propentofylline | 0.8 ± 0.12 | 1.1 ± 0.15 | 0.9 ± 0.18 |
| Morphine | 1.92 ± 0.14** | 1.85 ± 0.16** | 1.48 ± 0.2* |
| Morphine + Propentofylline | 1.3 ± 0.24# | 1.2 ± 0.22# | 1.1 ± 0.1# |

*p < 0.05 versus chronic saline group
**p < 0.01 versus chronic saline group
p < 0.05 versus chronic morphine-treated group

TABLE 3

Effect of Propentofylline (10 μg) on Chronic Morphine-Induced Upregulation of IL-1β, IL-6 and TNF-α Protein Levels at the L5 Lumbar Spinal Cord

| Treatment | IL-1β | IL-6 | TNF-α |
|---|---|---|---|
| Saline | 43.5 ± 5.4 | 197.3 ± 17 | 25.8 ± 2.8 |
| Propentofylline | 50.1 ± 7.8 | 178.6 ± 21 | 27.2 ± 3.18 |
| Morphine | 73.5 ± 9.2* | 359 ± 62.4* | 36.6 ± 5.6 |
| Morphine + Propentofylline | 56.4 ± 3.3# | 231 ± 46.72# | 29.4 ± 7.1 |

*p < 0.05 versus chronic saline group
p < 0.05 versus chronic morphine-treated group The activation of spinal glia, a characteristic response observed during central neuroimmune activation and neuroinflammation, may mediate and/or modulate the pathogenesis of persistent pain. Recent evidence has indicated that the glial cells modulate opioid action. Studies showed that morphine primes microglia for enhanced production of TNF-α and nitric oxide (NO), inhibits microglial chemotaxia, and induces apoptosis of microglial cells (Chao, C. C. et al. 1994. J. Pharmacol. Exp. Ther. 269:198-203; Chao, C. C. et al. 1997. J. Pharmacol. Exp. Ther. 281:998-1004; Magazine, H. I. et al. 1996. J. Immunol. 156:4845-4850; Hu, S. et al. 2002. Neuropharmacology 42:829-836). In addition, chronic morphine activates spinal and cortical glial activity (Beitner-Johnson, D. et al. 1993. J. Neurochem. 61:1766-01773; Song, P. And Z-Q. Zhao. 2001. Neurosci. Res. 39:281-286). Intrathecal administration of the HIV coat glycoprotein, gp120, a patent activator of microglia, reduced the analgesic effectiveness of morphine (Johnston, I. et al. 2003. J. Pain 4(S1):52). Morphine tolerance and its withdrawal-induced behavioral hyperalgesia/allodynia are associated with spinal microglial and astroglial activation (Raghavendra, V. et al. 2002. J. Neu-

*rosci.* 22:9980-9989). Therefore, the effects of propentofylline on morphine-induced withdrawal hyperalgesia and on morphine tolerance are consistent with what is known about the role of spinal microglial cells in these events.

Experiments were performed to determine how propentofylline-induced suppression of glial activation contribute to reduced behavioral hypersensitivity after nerve injury. In a preventative paradigm, 10 μg of propentofylline (Sigma) to male Sprague-Dawley rats in 40 μl of sterile saline, or saline vehicle alone was administered intrathecally (i.t.) by lumbar puncture at the L4/5 level under brief halothane anesthesia (n=6-8/group). Treatment began one hour prior to L5 spinal nerve transection and continued daily in the evening until day 4 or 12 post-transection. Rats received either an L5 spinal nerve transection or sham surgery on day 0. The development of mechanical allodynia was monitored as described above in the morning at approximately 15 hours post-propentofylline or saline injection. Rats were euthanized on day 4 or 12 post-transection and tissue was further processed by real time RT-PCR, Western blot, or immunohistochemistry for determination of levels and rate of synthesis of the glutamate transporters GLT-1 and GLAST.

The L5 spinal nerve transection model of mononeuropathy has been previously shown to induce robust mechanical allodynia in the ipsilateral hindpaw (Colburn et al. 1999). In the present experiments, rats receiving L5 spinal nerve transection displayed significantly greater paw withdrawals to a 12 g Von Frey filament starting at day 1 post-transection than normal animals (p<0.001, L5 saline rats as compared to sham saline rats). Daily treatment with propentofylline initiated one hour prior to transection robustly inhibited the development of mechanical allodynia at all time points (P<0.001, L5 saline rats as compared to L5 propentofylline treated rats). In addition, from day 5 onwards, the L5 spinal nerve transection group receiving propentofylline was no longer discernable from the normal group (P>0.05, normal rats as compared to L5 propentofylline treated rats for day 5, 7, 9 and 12). These results support and confirm previous findings demonstrating an anti-allodynic effect of propentofylline administration (Sweitzer et al. 2001) and clearly demonstrate that propentofylline reverses L5 spinal nerve transection-induced mechanical allodynia.

Tissues from these rats was harvested and real Time RT-PCR analysis of ipsilateral lumbar spinal cord was carried out in order to determine if propentofylline modulated glutamate transporter expression at the transcriptional level. No difference was observed in GLT-1 mRNA expression between sham and L5 spinal nerve transected groups at either time point. However, rats receiving daily intrathecal propentofylline expressed significantly increased levels of GLT-1 mRNA at day 4 (P<0.01 propentofylline treated as compared to sham-operated rats; P<0.001 propentofylline treated as compared to L5 nerve transected rats) and day 12 (P<0.05 propentofylline treated as compared to L5 nerve transected rats). GLAST mRNA levels in L5 spinal nerve transected rats were unchanged compared with sham operated rats. Propentofylline treatment led to a slight decrease in GLAST mRNA at day 4 compared to L5 spinal nerve transection alone, however this did not attain statistical significance. Therefore, the data show that propentofylline enhanced levels of GLT-1 mRNA in spinal cord tissue.

Immunoreactivity of the glutamate transporters, GLT-1 and GLAST, was assessed in spinal cord tissue in order to determine if propentofylline is capable of altering glutamate transporter protein levels in vivo. In the sham surgery group, staining for GLT-1 was observed diffusely in the gray matter of the spinal cord, with higher levels in laminae I and II. Twelve days after L5 spinal nerve transection, GLT-1 immunoreactivity was decreased on the side ipsilateral to the lesion. In contrast, propentofylline treated rats demonstrated no qualitative difference in GLT-1 between ipsilateral and contralateral dorsal horns. Therefore, the L5 spinal nerve injury-induced decrease in GLT-1 was abolished by propentofylline treatment, demonstrating that propentofylline restored GLT-1 and GLAST immunoreactivity in spinal cord.

GLAST immunoreactivity in sham surgery rats was almost exclusively localized to the upper dorsal horn laminae. After L5 spinal nerve transection, decreased GLAST was observed in the ipsilateral dorsal horn. Propentofylline treatment did not enhance GLAST immunoreactivity on the ipsilateral side.

In order to quantitatively determine the effects of propentofylline on glutamate transporter protein expression, we carried out western blot analysis of ipsilateral lumbar spinal cord. No change in GLT-1 protein was observed in the L5 spinal nerve transection group at day 4. A decrease in GLT-1 protein at day 12 post-transection as compared to sham operated rats was observed, although this did not reach statistical significance. Propentofylline-treated rats exhibited similar levels of GLT-1 protein as the sham control group at both time points. On day 12, however, GLT-1 protein was significantly elevated in injured rats receiving propentofylline compared to those receiving L5 spinal nerve transection alone (P<0.05 as compared to L5 nerve transected rats) indicating a role for GLT-1 in propentofylline-induced anti-allodynia.

GLAST protein levels exhibited a different pattern following injury and drug treatment. Four days after L5 spinal nerve transection, GLAST protein was significantly elevated above sham levels (P<0.001 as compared to sham operated rats), and by day 12, GLAST density trended towards being lower than in sham controls. There was a significant decrease in GLAST in the propentofylline group as compared with the saline-treated injured rats at day 4. (P<0.001 as compared to L5 nerve transected rats). These data indicate that there is differential modulation of GLT-1 and GLAST by propentofylline in a rodent neuropathic pain model.

Additional studies were carried out in cultured astrocytes. Astrocytes take on a characteristic polygonal morphology in culture which is considered to be a reactive or de-differentiated phenotype that is clearly seen in control (saline-treated) cells. Previously it has been demonstrated that the cAMP analogue dibutyryl-cAMP (db-cAMP) as well as epidermal growth factor (EGF), induce differentiation and maturation of cultured astrocytes (Schlag et al. 1998; Zelenaia et al. 2000). The adenylate cyclase activator, forskolin and EGF were used in cultured astrocytes as positive controls to induce differentiation. Propentofylline-treated astrocytes displayed a similar shift to a differentiated, process-bearing stellate phenotype after only 3 days. This finding indicated that high dose propentofylline induced differentiation of astrocytes; propentofylline was capable of drawing astrocytes from an activated, de-differentiated state to a differentiated phenotype that is capable of more effectively maintaining synaptic homeostasis.

Considered together, the data examining the mechanistic basis for propentofylline's anti-allodynia properties demonstrated that the drug differentially modulates spinal astrocytic glutamate transporters (GLT-1 and GLAST) in vivo. The modulation of glutamate transporter levels was shown to be related to the ability of propentofylline to modify astrocytes and induce differentiation. The fact that GLT-1 was the principal glutamate transporter affected by propentofylline treatment indicates that drugs targeting this mechanism would be potential treatments of neuropathic pain, in the same way that propentofylline has been shown to be effective. Thus, the present invention also contemplates development of drugs other than propentofylline that can target GLT-1 modulation and thus be used to treat neuropathic pain.

The data described above demonstrate the efficacy of propentofylline to both inhibit the development of opioid tolerance and to inhibit opioid withdrawal-induced hyperalgesia. Therefore, the present invention is a composition and method for inhibiting the development of opioid tolerance and opioid withdrawal-induced hyperalgesia in animals, including humans. The inhibition of development of tolerance and hyperalgesia in response to administration of opioids, such as morphine, results in the ability to administer lower doses of these analgesics to patients. The administration of lower doses is desired in order to minimize the development of opioid toxicity, a toxicity that can lead to life-threatening situations including death due to respiratory arrest. The present invention is a composition for inhibiting development of opioid tolerance and opioid withdrawal-induced hyperalgesia that comprises propentofylline and an opioid administered in a pharmaceutically acceptable vehicle. In a preferred embodiment the opioid of the present invention is morphine. The opioid, however, could include but not be limited to any opioid used clinically such as oxycodone, hydromorphone, long-acting Morphine preparations, fentanyl and its congeners, percoset, and percodan.

The method of the present invention is a method for inhibiting opioid tolerance and opioid withdrawal-induced hyperalgesia that comprises administering to a patient an effective amount of a composition of propentofylline and an opioid in a pharmaceutically acceptable vehicle so that opioid tolerance and opioid withdrawal-induced hyperalgesia are inhibited. The present invention is also a method for reducing the effective dose of an opioid in a patient comprising administering to the patient a composition comprising propentofylline and an opioid wherein the opioid is administered in a dose that is lower than a dose administered without propentofylline.

In a preferred embodiment, propentofylline would be administered to an animal, including a human, at the same time as the opioid chosen for therapy is administered. The pain being treated could be due to a variety of causes including but not limited to cancer, multiple sclerosis, low back pain associated with radiculopathy (root injury), HIV-associated neuropathy, diabetic neuropathy, trigeminal neuralgia, postherpetic neuralgia, phantom limb pain, or nerve injury due to surgery or trauma. The drugs would be administered in a pharmaceutically acceptable carrier either orally, intravenously, intramuscularly, subcutaneously, by infusion pump implanted subcutaneously, intrathecally, or any other applicable route of administration that would deliver the drug to the desired site of action. One of skill would understand how to formulate and deliver propentofylline and the opioids based on knowledge of the pharmacokinetics of the drug collected in patients treated for neurodegenerative diseases and the clinical studies that supported the development of the drug for neurodegenerative diseases. Thus, one of skill would understand how to make and use the instant invention based on their knowledge of the pharmacology and toxicology of opioid compounds for the treatment of pain. The opioid to be administered and the dose of the opioid would be chosen by one of skill in the art based upon their experience with opioid use in pain management therapy.

The following non-limiting examples are provided to further illustrate the instant invention.

EXAMPLES

Example 1

Behavioral Testing

Mechanical sensitivity was measured as the frequency of foot withdrawals elicited by a defined mechanical stimulus. Each rat, under unrestrained conditions, was placed beneath an inverted, ventilated Plexiglas cage upon an elevated aluminum screen surface with 1 cm mesh openings. Animals had been previously acclimated to the environment and the experimenter.

In blinded testing, rats were subjected to sequential series of 10 tactile stimulations to the dorsal surface of the ipsilateral hindpaw using 2 and 12 gauge von Frey filaments (Stoelting Co., WoodDale, Ill.) sequentially. The number of foot withdrawals to this normally non-noxious stimulus determined mechanical allodynia. Mechanical sensitivity was assessed by recording the total number of responses elicited during three successive trials separated by at least 10 minutes. The pressure required to elicit paw withdrawal, the paw pressure threshold was determined.

Thermal nociceptive thresholds were evaluated by the hot water tail-flick test that has been described previously (Bian, D. et al. 1999. *Brain Res.* 831:55-63). The test consisted of immersing the tail of the rats in water maintained at 49° C. and then recording the latency to a rapid flick. A 15 second cut-off time was used. Again, the total number of responses elicited during three successive trials separated by at least 10 minutes was recorded and then expressed as the % maximal possible effect. The tester was again blinded to the test groups.

Example 2

Real-Time PCR

Total RNA was treated with DNase I (Ambion, Austin, Tex.) to remove DNA contamination before cDNA synthesis. The reverse transcription (RT) was carried out in a 100 μl total reaction volume containing RT buffer, dNTPs, multiscribe reverse transcriptase, RNase-free water and 10 μg of DNase-treated total RNA. The RT reaction was carried out at 25° C. for 10 minutes, 37° C. for 120 minutes, and 95° C. for 5 minutes. Real-time PCR analysis was performed using gene-specific primers and probes that were designed and blasted against GENBANK to confirm their species and gene specificity. The primers and probes used were as follows: GFAP forward primer (5'-TGGCCACCAGTAACATGCAA-3'; SEQ ID NO:1), GFAP reverse primer (5'-CAGTTGGCGGC-GATAGTCAT-3'; SEQ ID NO:2, GFAP probe (5'-CA-GACGTTGCTTCCCGCAACGC-3'; SEQ ID NO:3), Mac-1 forward primer (5'-CTGCCTCAGGGATCCGTAAAG-3'; SEQ ID NO:4), Mac-1 reverse primer (5'-CCTCTGCCT-CAGGAATGACATC-3'; SEQ ID NO:5), Mac-1 probe (5'-CCCGGGACAATGCCGCGAA-3'; SEQ ID NO:6), GADPH forward primer (5'-CCCCCAATGTATCCGT-TGTG-3'; SEQ ID NO:7), GADPH reverse primer (5'-TAGC-CCAGGATGCCCTTTAGT-3'; SEQ ID NO:8) and GADPH PROBE (5'-TGCCGCCTGGAGAAACCTGCC-3'; SEQ ID NO:9). The primers and probes selected met the G-C content requirement and had a melting temperature of 60 and 70° C., respectively. The real-time PCR reactions were carried out using Platinum Taq DNA polymerase, 20 mM Tris HCl (pH 8.4), 50 mM KCl, 3 mM MgCl$_2$, 200 μM dGTP, dCTP, and dATP, 400 μM of dUTP and 1 U uracyl DNA glycosylase (UDG), 900 nM forward and reverse primers, 300 nM Taq-Man probe, and 10-fold dilution of cDNA (50 ng) from the RT step. Primers and probes for glyceraldehyde-3-phosphate (GADPH), GFAP and Mac-1 were obtained form Applied Biosystems (LaJolla, Calif.). The relative standard curves generated by plotting the threshold value versus the log of the amount of total cDNA added to the reaction (1-10000 pg) were used to compare the relative amount of target genes from control and chronic morphine-treated animals.

Example 3

RNase Protection Assay

Assessment of the temporal cytokine mRNA expression in the L5 lumber spinal cord was performed using a Ribonuclease Protection Assay technique. A Multiprobe RPAse kit was used (Pharmingen, San Diego, Calif.). Total RNA (15 μg) was hybridized to $^{32}$P-labeled antisense RNA probes transcribed using the rat cytokine-1 (rCK-1) multiprobe template set resulting in double-stranded target RNA. After Rnase digestion, protected RNA and probe were resolved on a denaturing polyacrylamide gel and visualized by overnight autoradiography. Quantitative image analysis was employed to compare mRNA levels based on band intensities for each cytokine. The intensity of each band was measured using image analysis software and assigned an arbitrary unit based on the measured intensity levels. The value for the normalized quantity for each band was obtained by dividing by the L32 house-keeping gene control. Individual mRNA concentration was calculated as the ratio of the expression compared with saline-treated animals in which normal values were weighted as 1.

Example 4

Cytokine Protein Estimation by ELISA

Quantitative determination of IL-1β, TNF-α and IL-6 protein was performed on the L5 spinal cord of the rats. Tissue homogenization was performed as previously described (Raghavendra, V. et al. 2002. *J. Neurosci.* 22:9980-9989). Briefly, weighed sections of L5 spinal cord were homogenized in a homogenization buffer consisting of a protease inhibitor using the a Power Gen 125 tissue tearer (Fisher Scientific, Suwanee, Ga.). Samples were spun at 20,000×g for 30 minutes at 4° C. Supernatant was aliquoted and stored at −80° C. for future protein quantification. IL-1β and TNF-α (R&D Systems, Minneapolis, Minn.) and IL-6 (Biosource, Camarillo, Calif.) protein concentrations were determined utilizing the quantitative sandwich enzyme immunoassay.

Example 5

Immunohistochemical Assessment of Glutamate Transporters

For assessment of GFAP, GLT-1 and GLAST immunoreactivity, a separate group of animals (n=4/treatment) were anesthetized and transcardially perfused with 0.1 M PBS (phosphate-buffered saline), pH 7.4, followed by 4% paraformaldehyde in PBS on day 12 post-L5 spinal nerve transection. Lumbar spinal cord sections were identified, isolated, and processed as described previously (Colburn et al. 1997). Free-floating, 20 μM were cut in a cryostat and processed for immunofluorescence. Sections were blocked with 5% FBS/0.1% Triton-X 100 for 1 h at room temperature (RT). For double immunofluorescence, spinal sections were incubated with a mixture of rabbit polyclonal anti-GLT-1 (1:500) or guinea pig anti-GLAST (1:5000), and mouse anti-GFAP G-A-5 (astrocyte marker, 1:400) in 3% FBS/0.1% triton-X 100/TBS over night at 4° C., washed, incubated in a mixture of goat anti-rabbit Alexa Fluor™-555 and goat anti-mouse Alexa Fluor™-488 (1:250, Molecular Probes, Eugene, Oreg.) secondary antibodies in 3% FBS/0.1% triton-X 100/TBS for 1 h at RT. To control for nonspecific staining, control sections were incubated in the absence of primary antibodies. The sections were examined with an Olympus fluorescence microscope, and images were captured with a Q-Fire cooled camera. Merged color images were processed using Adobe Photoshop (Adobe Systems, San Jose, Calif.).

Example 6

Isolation of mRNA and Protein from Spinal Cord

Tissue was collected from 4-5 rats/group on postoperative days 4 or 12. In order to obtain both mRNA and protein from the same tissue sample, the L5 region of the spinal cord (ipsilateral to the injury), was isolated and placed in PBS supplemented with protease inhibitor cocktail (1:1000, Sigma, St. Louis, Mo.) and RNase inhibitor (0.75 U/μL Ambion, Austin, Tex.). Samples were sonicated in five one-second bursts at half-maximal power, centrifuged at 6500 rpm for 15 minutes at 4° C. Protein-containing supernatants were collected and stored at −80° C. until further processing by Western blot analysis. The pellet was treated with TRIzol reagent (Invitrogen, Carlsbad, Calif.) for the extraction of total RNA according to the manufacturer's specifications.

Example 7

Real-Time RT-PCR

Total RNA was isolated from 60-80 mg of lumbar spinal cord tissue on post-transection days 4 or 12 as described above. RNA samples were subsequently treated with DNAsel (DNA-Free Kit, Ambion) to remove any contaminating genomic DNA. Reverse transcription (RT) was carried out using the high-capacity cDNA archive kit (Applied Biosystems, Foster City, Calif.) according to the vendor's protocol.

Real time RT-PCR reactions were carried out in a total reaction volume of 25 uL containing a final concentration of 1.5 U Platinum Taq DNA polymerase (Invitrogen); 20 mM Tris HCl (pH 8.4); 50 mM KCl; 3 mM MgCl$_2$; 200 uM dGTP, dCTP, and dATP; 400 uM dUTP and 1 U of UDG (uracyl DNA glycosylase); 900 nM of forward and reverse primers; 300 nM Taqman probe; and 5 uL of a 10-fold dilution of cDNA (50 ng) from the RT step. Primer and probe sequences for the genes of interest (GLT-1, GLAST and GAPDH) were [PLEASE PROVIDE]. The iCycler Multicolor Real-Time PCR detection system (Bio-Rad) was used to quantify PCR product. The fluorescence and threshold values obtained were used to compare the relative amount of target mRNA in experimental groups to those of controls (Livak and Schmittgen 2001). Each experiment was run twice and samples were run in duplicate. For each sample, the mean $C_T$ value for the control gene (GAPDH) was then subtracted from the mean $C_T$ value for the gene of interest (GLT-1, GLAST). The difference in the values for all animals in the control group (normal, s.c. saline) were then averaged and subtracted from the difference in the values for each animal in the experimental groups.

Example 8

Western Blot Analysis

Protein obtained from L5 lumbar spinal cord was quantified using the Lowry method (DC assay, Bio-Rad, Richmond, Calif.). Forty micrograms of protein and standard protein markers were subjected to SDS polyacrylamide gel electrophoresis (7.5% gel, Bio-Rad) and transferred to polyvinylidene difluoride (PVDF, Bio-Rad) filters. Nonspecific binding was blocked by incubation with 5% milk/PBS-T at room temperature for 1 hour followed by incubation overnight at 4 C with monoclonal guinea pig anti-GLT-1 or guinea pig anti-GLAST (1:2500, Chemicon). The following day, blots were washed and incubated for 1 hour at room temperature with goat anti-guinea pig HRP-conjugated secondary antibody (1:10,000 for GLAST and 1:100,000 for GLT-1, Sigma), visualized with SuperSignal West Femto Maximum Sensitivity Substrate (Pierce, Rockford, Ill.) for 1 minute and imaged using the Typhoon Imaging System (Amersham Biosciences, Piscataway, N.J.). Finally, blots were incubated for 15 minutes in stripping buffer (Pierce) and reprobed with a monoclonal mouse anti-beta-actin antibody (1:10,000, Abcam, Cambridge, Mass.) as a loading control. Densitometric analysis was performed using ImageQuant 5.2 (Molecular Dynamics, Amersham Biosciences, Piscataway, N.J.).

Example 9

Culture of Primary Astrocytes

Astrocyte cultures were prepared from the cortices of neonatal rats (1-3 day old) using the Worthington Papain Dissociation System (Worthington Biochemical Corporation, Lakewood, N.J.) as per the method of Huettner and Baughman (1986). Briefly, cortices of neonatal rats were dissected, treated with papain (20 U/ml), dissociated by titration and plated in 75 cm2 flasks in Dulbecco's modified Eagle's medium supplemented with 10% charcoal-stripped FBS and 1% penicillin/streptomycin (100 U/ml penicillin, 100 ìg/ml streptomycin). Cells were fed twice weekly until they reached confluence (Day 10-12 in vitro) at which point they were mechanically shaken for 1 hr on an orbital shaker to remove any remaining oligodendrocytes and microglia. Subsequently, cultures were treated with trypsin for 30 mins at 37 C and re-plated into 12-well dishes at a density of 150,000 cells/well (~3.0×104 cells/cm2).

After approximately 14 days (2 days after subplating into 12-well plates) astrocytes had formed a confluent monolayer. The culture medium was exchanged and replaced with fresh Dulbecco's modified Eagle's Medium (DMEM) containing 10% fetal bovine serum. Propentofylline (1000 ìM), forskolin (10 ìM), epidermal growth factor (EGF, 30 ng/ml) or saline was then added and cells were incubated for 3 days further at 37 C. Phase contrast microscopy was then carried out in order to assess the morphology of cells after the various treatments.

What is claimed is:

1. A pharmaceutical composition for inhibition of opioid tolerance and opioid withdrawal-induced hyperalgesia comprising:
   a) Propentofylline;
   b) an opioid drug; and
   c) a pharmaceutically acceptable carrier, and wherein said composition is administered intrathecally at a dose of Propentofylline of 10 micrograms.

2. The pharmaceutical composition of claim 1 wherein the opioid is morphine.

* * * * *

```
                        SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tggccaccag taacatgcaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
cagttggcgg cgatagtcat                                                   20

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
cagacgttgc ttcccgcaac gc                                                22

<210> SEQ ID NO 4
```

```
-continued

<211> LENGTH: 21
<212> TYPE: DNA
<213> ORGANISM: Artificial Sequence
<220> FEATURE:
<223> OTHER INFORMATION: Synthetic primer

<400> SEQUENCE: 4
ctgcctcagg gatccgtaaa g                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
cctctgcctc aggaatgaca tc                                             22

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
cccgggacaa tgccgcgaa                                                 19

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cccccaatgt atccgttgtg                                                20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
tagcccagga tgcccttag t                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
tgccgcctgg agaaacctgc c                                              21
```